(12) United States Patent
Bachovchin et al.

(10) Patent No.: US 7,998,997 B2
(45) Date of Patent: Aug. 16, 2011

(54) INHIBITORS OF FIBROBLAST ACTIVATION PROTEIN ALPHA

(75) Inventors: William W. Bachovchin, Cambridge, MA (US); Hung-Sen Lai, Andover, MA (US)

(73) Assignee: Trustees of Tufts College, Medford, MA (US)

( * ) Notice: Subject to any disclaimer, the term of this patent is extended or adjusted under 35 U.S.C. 154(b) by 58 days.

(21) Appl. No.: 11/994,707

(22) PCT Filed: Jul. 5, 2006

(86) PCT No.: PCT/US2006/026258
§ 371 (c)(1),
(2), (4) Date: Jul. 14, 2008

(87) PCT Pub. No.: WO2007/005991
PCT Pub. Date: Jan. 11, 2007

(65) Prior Publication Data
US 2009/0221818 A1    Sep. 3, 2009

Related U.S. Application Data

(60) Provisional application No. 60/696,772, filed on Jul. 5, 2005.

(51) Int. Cl.
*A61K 31/40* (2006.01)
*C07D 209/00* (2006.01)

(52) U.S. Cl. ........................................ 514/408; 548/400

(58) Field of Classification Search .................. 514/408; 548/400
See application file for complete search history.

(56) References Cited

U.S. PATENT DOCUMENTS

| | | | | |
|---|---|---|---|---|
| 4,935,493 A * | 6/1990 | Bachovchin et al. | ......... | 530/331 |
| 4,963,655 A | 10/1990 | Kinder et al. | | |
| 5,106,948 A | 4/1992 | Kinder et al. | | |
| 5,159,060 A * | 10/1992 | Kinder et al. | ................. | 530/331 |
| 7,399,869 B2 * | 7/2008 | Cohen et al. | ................. | 548/405 |
| 2005/0084490 A1 | 4/2005 | Adams et al. | | |

FOREIGN PATENT DOCUMENTS

| | | |
|---|---|---|
| WO | WO-03/092605 A2 | 11/2003 |
| WO | WO-2005/047297 A1 | 5/2005 |
| WO | WO-2006/125227 A2 | 11/2006 |

OTHER PUBLICATIONS

Adams, S. et al., "PT-100, a Small Molecule Dipeptidyl Peptidase Inhibitor, Has Potent Antitumor Effects and Augments Antibody-Mediated Cytotoxicity via a Novel Immune Mechanism", *Cancer Research*, 64(15):5471-5480 (Aug. 1, 2004).
Cheng, J. D. et al., "Abrogation of fibroblast activation protein enzymatic activity attenuates tumor growth", *Mol. Cancer Ther.*, 4(3):351-360 (Mar. 2005).
Coutts, S. J. et al., "Structure-Activity Relationships of Boronic Acid Inhibitors of Dipeptidyl Peptidase IV. 1. Variation of the $P_2$ Position of $X_{aa}$-boroPro Dipeptides", *J. Med. Chem.*, 39(39):2087-2094 (American Chemical Society, Washington, DC, USA, May 10, 1996).
Hu, Y. et al., "Synthesis and structure-activity relationship of N-alkyl Gly-boro-Pro inhibitors of DPP4, FAP, and DPP7", *Bioorg. Med. Chem. Lett.*, 15(19):4239-4242 (Pergamon, Elsevier Science, Great Britain, Oct. 1, 2005).
Kelly, T., "Fibroblast activation protein-α and dipeptidyl peptidase IV (CD26): Cell-surface proteases that activate cell signaling and are potential targets for cancer therapy", *Drug Resistance Updates*, 8(1-2):51-58 (Churchill Livingstone, Edinburgh, Great Britain, Feb. 1, 2005).
Tran, T. et al., "Synthesis and structure—activity relationship of N-acyl-Gly-, N-acyl-Sar- and N-blocked-boroPro inhibitors of FAP, DPP4, and POP", *Bioorg. Med. Chem. Lett.*, 17(5):1438-1442 (Pergamon, Elsevier Science, Great Gritian, Feb. 14, 2007).
Villhauer, E. B. et al., "1-[[(3-Hydroxy-1-adamantyl)amino]acetyl]-2-cyano-(S)-pyrrolidine: A Potent, Selective, and Orally Bioavailable Dipeptidyl Peptidase IV Inhibitor with Antihyperglycemic Properties", *J. Med. Chem.*, 46(13):2774-2789 (American Chemical Society, Washington DC, USA, Jan. 1, 2003).
Supplementary European Search Report dated Jun. 17, 2009.
International Search Report for PCT/US06/26258 mailed on Nov. 16, 2006.

* cited by examiner

*Primary Examiner* — Susannah Chung
(74) *Attorney, Agent, or Firm* — Alan W. Steele; Foley Hoag LLP

(57) ABSTRACT

Disclosed are peptide-based compounds that include boronic acid or cyano functionality, which efficiently and selectively inhibit fibroblast activation protein alpha. Among other therapeutic utilities, the peptide-based compounds may be useful for the treatment of cancer.

7 Claims, No Drawings

INHIBITORS OF FIBROBLAST ACTIVATION PROTEIN ALPHA

RELATED APPLICATIONS

This application claims the benefit of priority to Patent Cooperation Treaty Application number PCT/US2006/026258, filed Jul. 5, 2006; which claims the benefit of priority to U.S. Provisional Patent Application Ser. No. 60/696,772, filed Jul. 5, 2005.

BACKGROUND OF THE INVENTION

Fibroblast activation protein α (FAP α) is a dual-specificity dipeptidyl-peptidase and collagenase (Scanlan, M. J. et al. (1994), Proc. Natl. Acad. Sci. USA, 91, 5657-5661). FAP and the well-studied dipeptidyl-peptidase IV (DPP IV, EC 3.4.14.5) are both members of the recently described "DPP IV activity- and/or structure-homologues" (DASH) proteins, comprising enzymes with a common post-proline-cleaving serine dipeptidase mechanism (Sedo, A. and Malik, R. Biochim. Biophys. Acta 2001, 1550, 2, 107-116; P. Bušek, et al. Int. J. Biochem. Cell Biol. (2004) 36(3), 408-421). FAP has a high degree of homology with DPP-IV, and has been reported to form heterodimers with DPP IV ii vivo.

FAP differs from DPP IV in that its distribution is highly localized and it is not as abundant. Unlike DPP IV, FAP is a tumor-associated antigen that is not expressed in normal tissues; rather, it is only expressed on the tumor-supporting and non-malignant cells comprising the tumor stroma (Folkman, J., et al. Nature (1989) 339, 58-61; Garin-Chesa, P., et al., Proc. Natl. Acad. Sci. USA (1990), 87, 7235-7239; Chen W T, Adv Exp Med Biol (2003), 524, 197-203). There is strong evidence implicating FAP as a tumor stromal marker. FAPα is selectively expressed in reactive stromal fibroblasts of many histological types of human epithelial cancers, granulation tissue of healing wounds, and malignant cells of certain bone and soft tissue sarcomas. Normal adult tissues are generally devoid of detectable FAPα, but some fetal mesenchymal tissues transiently express the protein. In contrast, most of the common types of epithelial cancers, including >90% of breast, non-small-cell lung, and colorectal carcinomas, contain FAPα-reactive stromal fibroblasts (Scanlan et al., loc. cit.). These FAPα+ fibroblasts accompany newly formed tumor blood vessels, forming a distinct cellular compartment interposed between the tumor capillary endothelium and the basal aspect of malignant epithelial cell clusters (Welt et al. (1994) J. Clin. Oncol. 12(6), 1193-1203). While FAPα+ stromal fibroblasts are found in both primary and metastatic carcinomas, the benign and premalignant epithelial lesions tested (Welt et al., loc. cit.), such as fibroadenomas of the breast and colorectal adenomas, only rarely contain FAPα+ stromal cells. The expression profile of FAP suggests that it may play a role in the invasion of normal tissue by a cancerous growth, as well as in tumorigenesis. Therefore, a need exists for the design and synthesis of selective inhibitors of FAP.

SUMMARY OF THE INVENTION

One aspect of the invention relates to compounds having a structure of Formula (I)

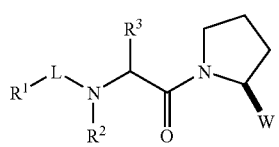

(I)

wherein
L is absent or is —XC(O)—;
$R^1$ is selected from H, $C_{1-6}$alkyl, $C_{1-6}$acyl, $C_{1-6}$aralkyl, $C_{1-6}$aracyl, $C_{1-6}$heteroaracyl, carbocyclyl, aryl, and $ArSO_2$—;
$R^2$ is selected from H and $C_{1-6}$alkyl, or $R^1$ and $R^2$ together are phthaloyl, thereby forming a ring;
$R^3$ is selected from H, $C_{1-6}$alkyl, $C_{1-6}$hydroxyalkyl, $C_{1-6}$thioalkyl, and $C_{1-6}$aralkyl;
W is selected from $B(Y^1)(Y^2)$ and CN;
$Y^1$ and $Y^2$ are independently selected from OH or a group that is hydrolyzable to give a boronic acid, or together with the boron atom to which they are attached form a 5- to 8-membered ring that is hydrolysable to a boronic acid;
X is selected from O and NH.

Another aspect of the invention relates to compounds having a structure of Formula II

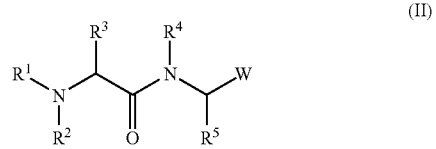

(II)

$R^1$ is selected from H, $C_{1-6}$alkyl, $C_{1-6}$acyl, $C_{1-6}$aralkyl, $C_{1-6}$aracyl, $C_{1-6}$heteroaracyl, carbocyclyl, and aryl;
$R^2$ is selected from H and $C_{1-6}$alkyl;
$R^3$ is selected from H, $C_{1-6}$allyl, $C_{1-6}$hydroxyalkyl, $C_{1-6}$thioalkyl, and $C_{1-6}$aralkyl;
$R^4$ is selected from H and $C_{1-6}$alkyl, or $R^3$ and $R^4$ together are $C_{1-6}$alkyl thereby forming a ring;
$R^5$ is selected from H, $C_{1-6}$alkyl, $C_{1-6}$hydroxyalkyl, $C_{1-6}$thioalkyl, and $C_{1-6}$aralkyl, or $R^4$ and $R^5$ together are $C_{1-6}$alkyl-S;
W is selected from H, $B(Y^1)(Y^2)$, and CN;
$Y^1$ and $Y^2$ are independently selected from OH or a group that is hydrolyzable to give a boronic acid, or together with the boron atom to which they are attached form a 5- to 8-membered ring that is hydrolysable to a boronic acid;
with the proviso that W can be H only when $R^4$ and $R^5$ together are $C_{1-6}$alkyl-S.

DETAILED DESCRIPTION OF THE INVENTION

The invention involves compounds useful as enzyme inhibitors. These compounds are generally useful as inhibitors of protease inhibitors, preferably they are inhibitors of FAP. While not wishing to be bound by any particular theory, it is observed that peptidyl-boronic acids have been well characterized with respect to their ability to inhibit serine proteases (Bristol L A, et al., Blood (1995), 85(12), 3602-9; Coutts, S. J., et al., (1996), J. Med. Chem. 39, 2087-2094). This inhibition may be attributed to the availability of an empty p-orbital on boron, which is well-suited to accept the lone pair of electrons on the oxygen of the active site serine residue. The resulting tetrahedral geometry of boron acts as a transition-state mimic of the natural, carbonyl-containing substrate. Because DPP IV and FAP are closely related structurally, it is presumed that boronic acid compounds are able to form stable tetrahedral intermediates with the active site serine of FAP, as they do with DPP IV.

In certain embodiments, compounds of the invention include stereocenters, wherein the stereochemistry can be (R) or (S). Regarding the assignment of absolute stereochemistry, the Cahn-Ingold-Prelog rules are followed. These rules are described, for example, in *Organic Chemistry*, Fox and Whitesell; Jones and Bartlett Publishers, Boston, Mass. (1994); Section 5-6, pp 177-178, which section is hereby incorporated by reference. Peptides can have a repeating backbone structure with side chains extending from the backbone units. Generally, each backbone unit has a side chain associated with it, although in some cases, the side chain is a hydrogen atom. In other embodiments, not every backbone unit has an associated side chain.

One aspect of the invention relates to compounds having a structure of Formula (I)

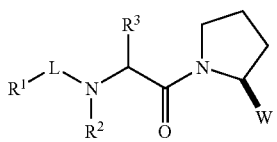

wherein
L is absent or is —XC(O)—;
$R^1$ is selected from H, $C_{1-6}$alkyl, $C_{1-6}$acyl, $C_{1-6}$aralkyl, $C_{1-6}$aracyl, $C_{1-6}$heteroaracyl, carbocyclyl, aryl, and $ArSO_2$—;
$R^2$ is selected from H and $C_{1-6}$alkyl, or $R^1$ and $R^2$ together are phthaloyl, thereby forming a ring;
$R^3$ is selected from H, $C_{1-6}$alkyl, $C_{1-6}$hydroxyalkyl, $C_{1-6}$thioalkyl, and $C_{1-6}$aralkyl, preferably $R^3$ is H or $C_{1-6}$alkyl, more preferably $R^3$ is H;
W is selected from $B(Y^1)(Y^2)$ and CN, preferably W is $B(Y^1)(Y^2)$;
$Y^1$ and $Y^2$ are independently selected from OH or a group that is hydrolyzable to give a boronic acid, or together with the boron atom to which they are attached form a 5- to 8-membered ring that is hydrolysable to a boronic acid, preferably $Y^1$ and $Y^2$ are OH;
X is selected from O and NH, preferably X is NH.

In certain embodiments, L is absent; and $R^1$ is selected from H, $C_{1-6}$alkyl, $C_{1-6}$acyl, $C_{1-6}$aralkyl, $C_{1-6}$aracyl, $C_{1-6}$heteroaracyl, carbocyclyl, aryl, and $ArSO_2$—. In certain such embodiments, L is absent; and $R^1$ is $C_{1-6}$alkyl selected from methyl, ethyl, isopropyl, and tert-butyl. In certain such embodiments, L is absent; and $R^1$ is $C_{1-6}$acyl selected from acetyl and pivaloyl. In certain such embodiments, L is absent; and $R^1$ is phenylmethyl. In certain such embodiments, L is absent; and $R^1$ is aracyl selected from 2-phenylethylcarbonyl, phenylmethylcarbonyl, (1-naphthyl)carbonyl, and (2-naphthyl)carbonyl, and (4-sulfamoylphenyl)carbonyl. In certain embodiments, L is absent; and $R^1$ is pyrazyl. In certain embodiments, L is absent; and $R^1$ carbocyclyl selected from cyclohexyl and adamantyl. In certain embodiments, L is absent; and $R^1$ is selected from phenyl and phenylsulfonyl.

In certain embodiments, L is —XC(O)—, X is O, and $R^1$ is $C_{1-6}$aralkyl. In certain such embodiments L is —XC(O)—, X is O, and $R^1$ is phenylmethyl.

In certain embodiments, L is —XC(O)—, X is NH, and $R^1$ is selected from aryl and $C_{1-6}$aralkyl. In certain embodiments, L is —XC(O)—, X is NH, and $R^1$ is selected from phenyl and phenylmethyl.

In certain embodiments, $R^2$ is $C_{1-6}$alkyl. In preferred embodiments, $R^1$ is selected from methyl, isopropyl, and t-butyl. In more preferred embodiments, $R^1$ is methyl.

Another aspect of the invention relates to compounds having a structure of Formula II

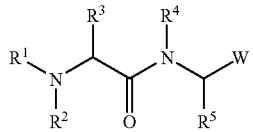

$R^1$ is selected from H, $C_{1-6}$alkyl, $C_{1-6}$acyl, $C_{1-6}$aralkyl, $C_{1-6}$aracyl, $C_{1-6}$heteroaracyl, and carbocyclyl, preferably $R^1$ is $C_{1-6}$aracyl or $C_{1-6}$acyl;
$R^2$ is selected from H and $C_{1-6}$alkyl, preferably $R^2$ is H;
$R^3$ is selected from H, $C_{1-6}$alkyl, $C_{1-6}$hydroxyalkyl, $C_{1-6}$thioalkyl, and $C_{1-6}$aralkyl, preferably $R^3$ is H;
$R^4$ is selected from H and $C_{1-6}$alkyl, preferably $R^4$ is H, or $R^3$ and $R^4$ together are $C_{1-6}$alkyl thereby forming a ring;
$R^5$ is selected from H, $C_{1-6}$alkyl, $C_{1-6}$hydroxyalkyl, $C_{1-6}$thioalkyl, and $C_{1-6}$aralkyl, preferably $C_{1-6}$alkyl, or $R^4$ and $R^5$ together are $C_{1-6}$alkyl-S—$C_{1-6}$alkyl;
W is selected from H, $B(Y^1)(Y^2)$, and CN, preferably W is $B(Y^1)(Y^2)$;
$Y^1$ and $Y^2$ are independently selected from OH or a group that is hydrolyzable to give a boronic acid, or together with the boron atom to which they are attached form a 5- to 8-membered ring that is hydrolysable to a boronic acid;
with the proviso that W can be H only when $R^4$ and $R^5$ together are $C_{1-6}$alkyl-S—$C_{1-6}$alkyl.

In certain embodiments, $R^1$ is selected from $C_{1-6}$acyl and $C_{1-6}$aracyl. In preferred embodiments, $R^1$ is selected from phenylcarbonyl, (1-naphthyl)carbonyl, and acetyl.

In certain embodiments, $R^5$ is $C_{1-6}$alkyl. In preferred embodiments, $R^W$ is selected from methyl and ethyl.

In certain embodiments, W is H; and $R^4$ and $R^5$ together are $C_{1-6}$alkyl-S—$C_{1-6}$alkyl. In preferred embodiments, W is H; and $R^4$ and $R^5$ together are $C_2$alkyl-S—$C_1$alkyl, thereby forming a five-membered ring.

In certain embodiments, $R^3$ and $R^4$ together are $C_{1-6}$alkyl thereby forming a ring. In preferred such embodiments, $R^3$ and $R^4$ together are $C_2$alkyl, thereby forming a five-membered ring.

Another aspect of the invention relates to a method for the treatment of cancer, comprising administering a therapeutically effective amount of a compound of formula I or II. In preferred embodiments, the cancer is selected from human epithelial cancers, such as breast, non-small-cell lung, and colorectal carcinoma, and soft tissue sarcomas.

Another aspect of the invention relates to the use of a compound of formula I or II in the manufacture of a medicament for the treatment of cancer. In preferred embodiments, the cancer is selected from human epithelial cancers, such as breast, non-small-cell lung, and colorectal carcinoma, and soft tissue sarcomas.

Another aspect of the invention relates to pharmaceutical compositions, comprising a compound of formula I or II; and a pharmaceutically acceptable diluent or carrier.

DEFINITIONS

The term "$C_{1-6}$acyl" is art-recognized and refers to a $C_{1-6}$alkyl group wherein the point of attachment is a carbonyl group. $C_{1-6}$acyl can be represented generally by the formula $C_{1-5}$alkyl-C(O)—.

The term "$C_{1-6}$aracyl" can be represented generally by the formula aryl-$C_{1-5}$alkyl-C(O)—.

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups, such as trifluoromethyl and 2,2,2-tirfluoroethyl, etc. $C_0$ allyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "$C_{1-6}$aralkyl", as used herein, refers to a $C_{1-6}$alkyl group substituted with an aryl group.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls.

The term "carbonyl" is art-recognized and includes such moieties as can be represented by the general formula:

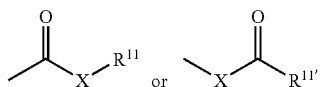

wherein X is a bond or represents an oxygen or a sulfur, and $R^{11}$ represents a hydrogen, an alkyl, an alkenyl, —$(CH_2)_m$—$R^8$ or a pharmaceutically acceptable salt, $R^{11'}$ represents a hydrogen, an alkyl, an alkenyl or —$(CH_2)_m$—$R^8$, where m and $R^8$ are as defined above. Where X is an oxygen and $R^{11}$ or $R^{11'}$ is not hydrogen, the formula represents an "ester". Where X is an oxygen, and $R^{11}$ is a hydrogen, the formula represents a "carboxylic acid".

As used herein, "enzyme" can be any partially or wholly proteinaceous molecule which carries out a chemical reaction in a catalytic manner. Such enzymes can be native enzymes, fusion enzymes, proenzymes, apoenzymes, denatured enzymes, farnesylated enzymes, ubiquitinated enzymes, fatty acylated enzymes, gerangeranylated enzymes, GPI-linked enzymes, lipid-linked enzymes, prenylated enzymes, naturally-occurring or artificially-generated mutant enzymes, enzymes with side chain or backbone modifications, enzymes having leader sequences, and enzymes complexed with non-proteinaceous material, such as proteoglycans, proteoliposomes. Enzymes can be made by any means, including natural expression, promoted expression, cloning, various solution-based and solid-based peptide syntheses, and similar methods known to those of skill in the art.

The terms "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, triazole, pyrazole, pyridine, pyrazine, pyridazine and pyrimidine, and the like.

The term "$C_{1-6}$heteroaracyl" as used herein refers to a $C_{1-6}$acyl group, wherein the alkyl portion is substituted with a heteroaryl group.

The term "heteroatom" as used herein means an atom of any element other than carbon or hydrogen. Preferred heteroatoms are nitrogen, oxygen, phosphorus, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms. The term terms "heterocyclyl" or "heterocyclic group" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "$C_{1-6}$heterocycloalkyl" refers to a $C_{1-6}$alkyl group substituted with a heterocyclic group.

As used herein, the term "inhibitor" is meant to describe a compound that blocks or reduces an activity of an enzyme (for example, inhibition of proteolytic cleavage of standard fluorogenic peptide substrates such as Suc-LLVY-AMC, Box-LLR-AMC and Z-LLE-AMC, inhibition of various catalytic activities of the 20S proteasome). An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme.

The terms "polycyclyl" or "polycyclic" refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings". Each of the rings of the polycycle can be substituted or unsubstituted.

The term "preventing" is art-recognized, and when used in relation to a condition, such as a local recurrence (e.g., pain), a disease, such as cancer, a syndrome complex, such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the hetero atoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "$C_{1-6}$thioalkyl" refers to an alkyl group substituted with a thiol group.

As used herein, the term "treating" or "treatment" includes reversing, reducing, or arresting the symptoms, clinical signs, and underlying pathology of a condition in manner to improve or stabilize a subject's condition.

Administration

Inhibitors prepared as described herein can be administered in various forms, depending on the disorder to be treated and the age, condition, and body weight of the patient, as is well known in the art. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent, or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses.

The precise time of administration and/or amount of the inhibitor that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotopic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", *J. Pharm. Sci.* 66:1-19)

In other cases, the inhibitors useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol, and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an inhibitor(s) with the carrier and, optionally, one or more accessory ingredients. In general, the formulations are prepared by uniformly and intimately bringing into association a ligand with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes, and the like, each containing a predetermined amount of an inhibitor(s) as an active ingredient. A compound may also be administered as a bolus, electuary or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants, such as wetting agents, emulsifying and suspending agents, sweetening, flavoring, coloring, perfuming, and preservative agents.

Suspensions, in addition to the active inhibitor(s) may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to inhibitor(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to an inhibitor(s), excipients, such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

The inhibitor(s) can be alternatively administered by aerosol. This result is accomplished by preparing an aqueous aerosol, liposomal preparation, or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins, like serum albumin, sorbitan esters, oleic acid, lecithin, amino acids, such as glycine, buffers, salts, sugars, or sugar alcohols. Aerosols generally are prepared from isotonic solutions.

Transdermal patches have the added advantage of providing controlled delivery of an inhibitor(s) to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the peptidomimetic in a polymer matrix or gel.

Ophthalmic formulations, eye ointments, powders, solutions, and the like, are also contemplated as being within the scope of this invention.

Pharmaceutical compositions of this invention suitable for parenteral administration comprise one or more inhibitors(s) in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of inhibitor(s) in biodegradable polymers, such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the inhibitors(s) of the present invention are administered as pharmaceuticals to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of agents may be given orally, parenterally, topically, or rectally. They are of course given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

These inhibitors(s) may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the inhibitor(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The invention now being generally described, it will be more readily understood by reference to the following examples which are included merely for purposes of illustration of certain aspects and embodiments of the present invention, and are not intended to limit the invention.

EXAMPLES

Chemistry

The syntheses of the dipeptide boronates described here were accomplished by adaptation of the synthetic methods described in Schemes 1-5. The pinanediol ester of proline boronic acid was coupled with an N-Boc protected amino acid in the presence of HATU. Removal of the N-Boc protection group and subsequent N-acylation resulted in the dipeptide boronate ester. Deprotection of the boronic acid moiety was accomplished using $BCl_3$. The reaction was then worked up and the desired product purified by reverse-phase HPLC.

Compounds 7-11 were synthesized according to Scheme 1 from commercially available N-acylated glycine derivatives 7a-11a. These N-acylated glycine derivatives were coupled with L-proline pinane boronic ester hydrochloride (boroPro-Pn) (1), followed by removal of the pinane protection group to give the desired compounds (7-11) in good yield (70-80%).

Scheme 1.

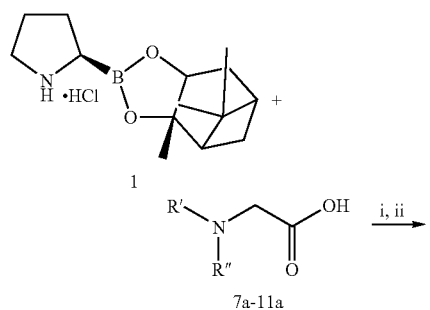

7a-11a

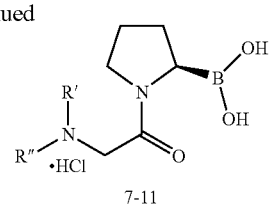

7-11

Reagents and conditions: i: HATU, DIPEA, DMF, 0° C. to rt.; ii: $BCl_3$, $CH_2Cl_2$, -78° C., 70-80% yield from 1.

Syntheses of compounds (12-19) bearing alkyl side chains at the N-terminus of the glycinyl-boroPro parent compound were accomplished by a strategy different from that described above (Scheme 2). First bromo-acetyl bromide was reacted with (1) to give the corresponding bromo-acetyl compound (2). Subsequent displacement of the acetyl bromines with appropriate amines, followed by the removal of the pinane groups gave the target compounds (12-19) with overall yield of 40-50%.

Scheme 2.

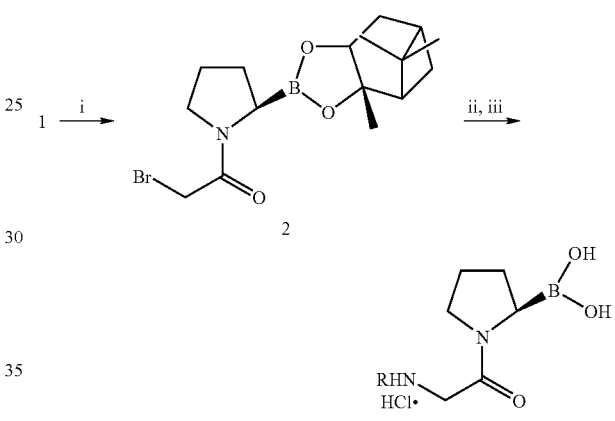

Reagents and conditions: i: $BrCH_2COBr$, DIPEA, $CH_2Cl_2$, 0° C. to rt., 90% yield; ii: $RNH_2$, $CH_2Cl_2$, rt.; iii: $BCl_3$, $CH_2Cl_2$, -78° C., 55-65% yield from 2.

As illustrated by Scheme 3, N-Boc-Glycine (3) was coupled with (1) to give the N-protected dipeptide (4) (obtained in 90% yield). Concurrent removal of the two protection groups with $BCl_3$ gave (6) (the desired compound, 77% total yield). Selective removal of the Boc group using 4 N HCl in dioxane at room temperature gave rise to H-Gly-L-boro-ProPn hydrochloride (5) in quantitative yield. The rest of the target compounds shown in Scheme 3 (20-29) were prepared by one of the three methods, differing from those described above primarily in the choice of acylated reagents, which varied from acyl or sulfonyl chlorides (Method A), carboxylic acids (Method B), to 4-nitrophenyl esters (Method C). Syntheses of compounds 20-25 proceeded smoothly with the reaction of 5 and the acyl or sulfonyl chlorides, followed by deprotection by $BCl_3$, with 50-60% yields in two steps (Scheme 3, Method A). Compounds 26 and 27 were synthesized via the coupling of 5 with the corresponding carboxylic acids, followed by deprotection, resulted in a 55-60% yield in two steps (Scheme 3, Method B). In contrast, compounds 28 and 29 were prepared via the acylation of 5 with 4-nitrophenyl N-benzyl (or N-phenyl) carbamates with subsequent deprotection. The overall yields in two steps were about 45-55% (Scheme 3, Method C). Following standard coupling procedures documented in the literature, compound 30a was condensed with L-Pro-CN and thiazolidine to give 30 and 31, respectively (Kienhofer, A. Synlett (2001), (11), 1811-1812; Speicher, A. et al. Journal fuer Praktische Chemie/Chemiker-Zeitung (1998), 340(6), 581-583).

Scheme 3.

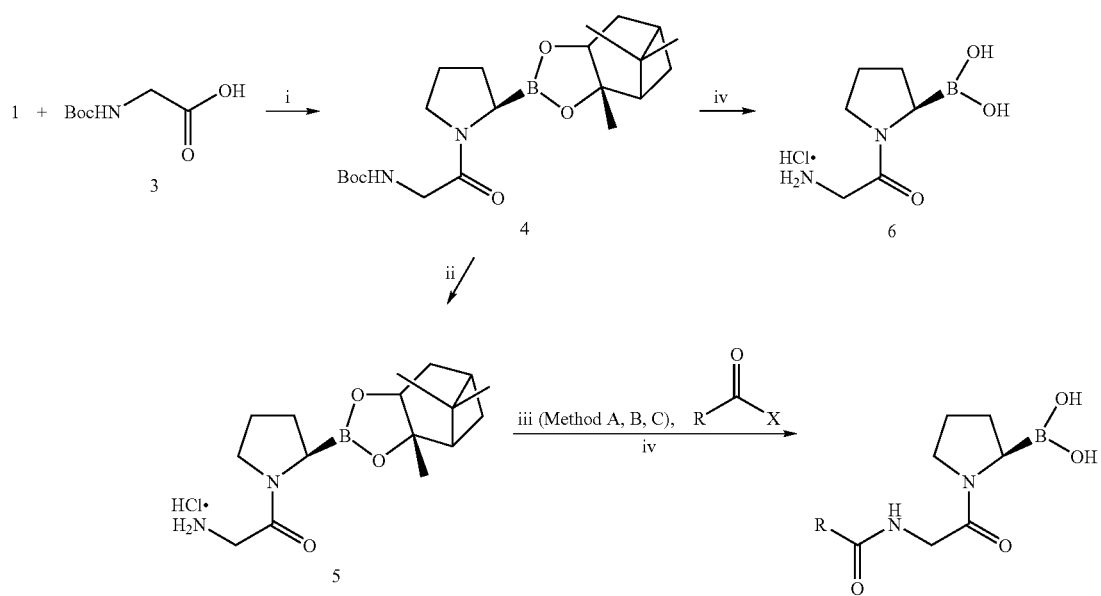

Reagents and conditions: i: HATU, DIPEA, DMF, 0° C. to rt., 90% yield; ii: 4N HCl in dioxane, rt., 100% yield; iii: (Method A: X = Cl, DIPEA, CH₂Cl₂, 0° C. to rt.; Method B: X = OH, DIPEA, EDCI, CH₂Cl₂, 0° C. to rt.; Method C: X= 4-OC₆H₄NO₂, DIPEA, CH₂Cl₂, 0° C. to rt.); iv: BCl₃, CH₂Cl₂, -78° C.; 45-60% yield for 20-29 from 5, 85% yield for 6 from 4.

Compound 32 resulted from the condensation of 32a and 1, followed by deprotection with BCl₃ with a 75% yield (Scheme 4).

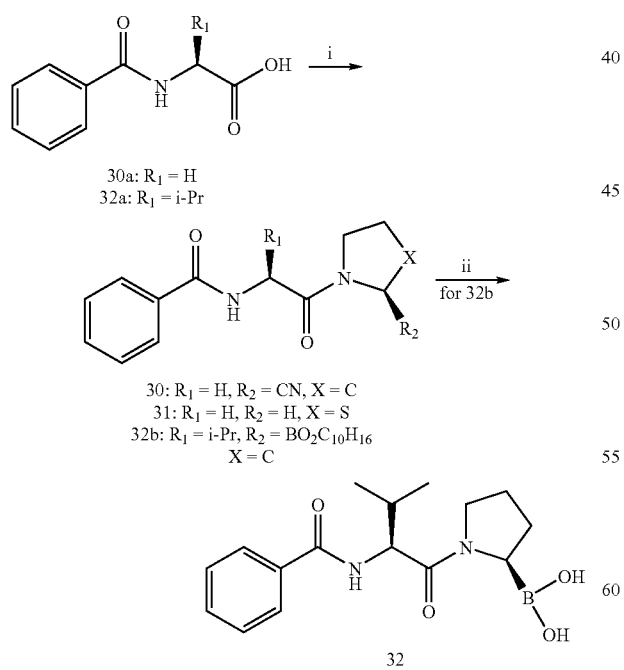

Reagents and conditions: i: L-Pro-CN (for 30), thiazolidine (for 31), 1(for 32b), HATU, DIPEA, DMF, 0° C to rt., 80-89% yield; ii: BCl₃, CH₂Cl₂, -78°C., 87% yield.

Another series of N-acyl dipeptides bearing boroalanine or boroethylglycine (33-36) were prepared as outlined in Scheme 5. N-(1-naphthalenyl)-glycine (33a) was coupled to L-boroAla-Pn-HCl (33b) or L-boroEthylGly-Pn-HCl (34b), followed by the pinane group removal with BCl₃ to give the corresponding target compounds 33 or 34 in 55-60% yields. Similar procedures were applied to generate 35 and 36 starting from N-acetyl-L-valine (35a) in 50-55% yield. The N-acetylated D-γ-lactam-L-boroAla (37) was prepared from acetylation of the amino lactam boronate (37a) using Ac₂O/Py under standard conditions in 85% yield (Scheme 6)(Ojima, I., et al., J. Am. Chem. Soc. (1987), 109(6), 1798-805).

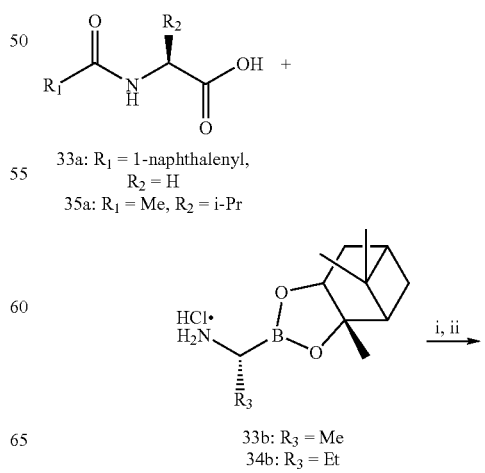

-continued

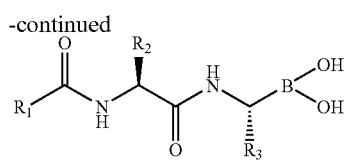

33: $R_1$ = 1-naphthalenyl, $R_2$ = H, $R_3$ = Me
34: $R_1$ = 1-naphthalenyl, $R_2$ = H, $R_3$ = Et
35: $R_1$ = Me, $R_2$ = i-Pr, $R_3$ = Me
36: $R_1$ = Me, $R_2$ = i-Pr, $R_3$ = Et Reagents and conditions: i: HATU, DIPEA, DMF, 0° C. to rt., ii: $BCl_3$, $CH_2Cl_2$, -78° C., 50-60% yield for two steps.

Biology

The enzymatic activity of purified FAP was measured at 25° C. on a Molecular Devices SPECTRAmax 340PC384 microtiter plate reader by monitoring the absorbance of H-Ala-Pro-pNA (Bachem) as the chromogenic substrate at 410 nm. The reaction mixture consisted of 3.5 mM substrate, approximately 1 nM FAP, 20 mM TRIS-HCl, 20 n1M KCl buffer at pH 7.4, and the inhibitor (ranging between $10^{-2}$ and $10^{-8}$ mM) in a total volume of 310 µL. Assays and their corresponding measurements were performed in duplicate. The $IC_{50}$ for each inhibitor was computed under conditions where the inhibitor was pre-incubated for 10 min with the enzyme at 25° C. prior to addition of the substrate. Inhibitor stock solutions (1 mM) were prepared in HCl solution (pH 2.0), and stored at -20° C. Stock solutions were diluted with 20 mM TRIS-HCl, KCl (20 mM) buffer at pH 7.4 immediately preceding the experiment according to the protocol. The results are shown below in Table 1.

TABLE 1

| Compound No. | R | $IC_{50}$ FAP (pH 7.4) | $IC_{50}$ DPP IV (pH 8.0) |
|---|---|---|---|
| 6 | $NH_2$— | 15 µM | 6.9 µM |
| 7 | acetamide | 88 nM | >34 µM |
| 8 | benzamide | 29 nM | |
| 9 | benzyl carbamate | 24 nM | >32 µM |
| 10 | phthalimide | 0.15 µM | |
| 11 | N,N-dimethylbenzamide | 0.46 µM | |
| 12 | dimethylamine | no inhib. | 560 µM |
| 13 | N-ethyl-N-methylamine | 4 mM | 46 µM |
| 14 | N-benzyl-N-methylamine | 15 µM | 69 µM |

TABLE 1-continued

| Compound No. | R | IC$_{50}$ FAP (pH 7.4) | IC$_{50}$ DPP IV (pH 8.0) |
| --- | --- | --- | --- |
| 15 | isopropyl-NH- | 990 nM | 900 nM |
| 16 | cyclohexyl-NH- | 340 nM | 940 nM |
| 17 | tert-butyl-NH- | 400 nM | 43 nM |
| 18 | 1-adamantyl-NH- | 110 nM | 110 nM |
| 19 | phenyl-NH- | 1.9 μM | 18 μM |
| 20 | (CH$_3$)$_3$C-C(O)-NH- | 0.28 μM | |
| 21 | naphthalen-1-yl-C(O)-NH- | 1.8 nM | |
| 22 | naphthalen-2-yl-C(O)-NH- | 10 nM | |
| 23 | Ph-CH$_2$CH$_2$-C(O)-NH- | 44 nM | |
| 24 | Ph-CH$_2$-C(O)-NH- | 29 nM | |
| 25 | Ph-S(O)$_2$-NH- | 34 nM | |

TABLE 1-continued

| Compound No. | R | IC$_{50}$ FAP (pH 7.4) | IC$_{50}$ DPP IV (pH 8.0) |
|---|---|---|---|
| 26 | pyrazine-2-carboxamide-N-methyl | 82 nM | |
| 27 | 4-sulfamoylbenzamide-N-methyl | 20 nM | |
| 28 | N-benzyl-N'-methylurea | 7.2 nM | |
| 29 | N-phenyl-N'-methylurea | 7.1 nM | |
| 30 | benzoyl-Gly-(2S)-cyanopyrrolidine | 2.2 μM | |
| 31 | benzoyl-Gly-thiazolidine | 14 μM | |
| 32 | benzoyl-Val-pyrrolidine-2-boronic acid | 30 μM | |
| 33 | naphthoyl-Gly-(1-aminoethyl)boronic acid | 8.2 μM | |
| 34 | naphthoyl-Gly-(1-aminopropyl)boronic acid | 9.0 μM | |

TABLE 1-continued

| Compound No. | R | IC$_{50}$ FAP (pH 7.4) | IC$_{50}$ DPP IV (pH 8.0) |
|---|---|---|---|
| 35 | ![structure] | no inhib. | |
| 36 | ![structure] | no inhib. | |

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound having a structure of formula (I)

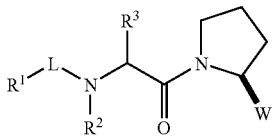

(I)

wherein
L is absent;
R$^1$ is C$_{1-6}$heteroaracyl;
R$^2$ is selected from the group consisting of H and C$_{1-6}$alkyl;
R$^3$ is selected from the group consisting of H, C$_{1-6}$alkyl, C$_{1-6}$hydroxyalkyl, C$_{1-6}$thioalkyl, and C$_{1-6}$aralkyl;
W is B(Y$^1$)(Y$^2$); and
Y$^1$ and Y$^2$ are independently OH.

2. The compound of claim 1, wherein R$^3$ is C$_{1-6}$alkyl.

3. The compound of claim 1, wherein C$_{1-6}$heteroaracyl is a C$_{1-6}$acyl substituted with a heteroaryl selected from the group consisting of pyrrole, furan, thiophene, imidazole, oxazole, thiazole, triazole, pyrazome, pyridine, pyrazine, pyridazine, and pyrimidine.

4. The compound of claim 1, wherein R$^2$ is H; and R$^3$ is C$_{1-6}$alkyl.

5. The compound of claim 1, wherein C$_{1-6}$heteroaracyl is a —C(O)-heteroaryl, wherein heteroaryl is selected from the group consisting of pyrrole, furan, thiophene, imidazole, oxazole, thiazole, triazole, pyrazome, pyridine, pyrazine, pyridazine, and pyrimidine.

6. A pharmaceutical composition suitable for administration to a patient, comprising a compound of claim 1; and a pharmaceutically acceptable diluent or carrier.

7. A pharmaceutical composition suitable for administration to a patient, comprising a compound of claim 5; and a pharmaceutically acceptable diluent or carrier.

* * * * *

UNITED STATES PATENT AND TRADEMARK OFFICE
CERTIFICATE OF CORRECTION

| | | |
|---|---|---|
| PATENT NO. | : 7,998,997 B2 | Page 1 of 1 |
| APPLICATION NO. | : 11/994707 | |
| DATED | : August 16, 2011 | |
| INVENTOR(S) | : Bachovchin et al. | |

It is certified that error appears in the above-identified patent and that said Letters Patent is hereby corrected as shown below:

Col. 24, in claim 3, at line 29, please replace "pyrazome" with --pyrazole--.

Col. 24, in claim 5, at line 37, please replace "pyrazome" with --pyrazole--.

Signed and Sealed this
Seventeenth Day of April, 2012

David J. Kappos
*Director of the United States Patent and Trademark Office*